US005693492A

United States Patent [19]

Cully et al.

[11] Patent Number: 5,693,492
[45] Date of Patent: Dec. 2, 1997

[54] DNA ENCODING GLUTAMATE GATED CHLORIDE CHANNELS

[75] Inventors: Doris F. Cully, Scotch Plains; Joseph P. Arena, West Orange; Philip S. Paress, Maplewood; Ken K. Liu, Laurence Harbor, all of N.J.

[73] Assignee: Merck & Co., Inc., Rahway, N.J.

[21] Appl. No.: 435,933

[22] Filed: May 5, 1995

[51] Int. Cl.$^6$ .............................. C12N 1/20; C12N 15/00; C07H 21/04

[52] U.S. Cl. .................. 435/69.1; 435/320.1; 435/252.33; 435/7.1; 435/7.2; 435/7.8; 435/252.3; 536/23.5; 536/23.1; 530/350; 514/2; 514/12; 935/19; 935/52

[58] Field of Search .................. 435/69.1, 252.3, 435/252.33, 320.1, 7.1, 7.2, 7.8; 536/23.5, 23.1; 530/350; 514/2, 12; 935/52, 19

[56] References Cited

U.S. PATENT DOCUMENTS 5,385,831  1/1995  Mulvihill et al. .

FOREIGN PATENT DOCUMENTS

WO 92/22652  12/1992  WIPO .
WO 93/07161   4/1993  WIPO .

OTHER PUBLICATIONS

Masood et al (1994) Mol. Pharmacol. vol. 45, 324–329.
Ultsch et al (1993) FEBS. vol. 324 (2), 171–177.
Arena, J., et al., Expression of a glutamate-activated chloride current in Xenopus oocytes injected with Caenorhabditis elegans RNA: evidence for moculation by avermectin, Molecular Brain Research, 15, pp. 339–348. (1992).
Ffrrench–Constant, R., et al. Molecular cloning and transformation of cyclodiene resistance in Drosophila: An Invertebrate y–aminobutyric acid subtype A receptor locus, Proc. Nat. Acad. Sci. USA, vol. 88, pp. 7209–7213. (1991).
Ffrench–Constant, R, et al. A point mutation in a Drosophila GABA receptor confers insecticide resistance, Nature, vol. 363, pp. 449–451. (1993).

Henderson, J. et al., Characterization of a putative y–aminobutyric acid (gaba) receptor B subunit gene from Drosophila melanogaster, vol. 193, No. 2, pp. 474–482. (1993).
Thompson, M. et al., Cloning and sequencing of the cyclodiene insecticide resistance gene from the yellow fever mosquito Aedes aegypti, vol. 325, No. 3, pp. 187–1090. (1993).
Arena, J. et al., Avermectin–sensitive chloride currents induced by caenorhabditis elegans RNA in xenopus oocytes, Molecular Pharm., 40, pp. 368–374. (1991).
Harvey, R. et al., Sequence of functional invertebrate GABAA receptor subunit which can form a chimeric receptor with a vertebrate a subunit, The EMBO Jour., vol. 101, No. 11 pp. 3239–3245. (1991).
Hutton, M. L. et al., A novel invertebrate GABAA receptor–like polypeptide sequence and pattern of gene expression, FEBS 12670, vol. 326, No. 1,2,3, pp. 112–116. (1993).
Zaman, S. et al., Unusual effects of benzodiazepines and cyclodiene insecticides on an expressed invertebrate GABAA receptor, FEBS 11356, vol. 307, No. 3, pp. 351–354. (1992).
Hollmann, et al., Cloning by functional expressing of a member of the glutamate receptor family, Nature, vol. 342, pp. 643–648. (1989).

*Primary Examiner*—Paula K. Hutzell
*Assistant Examiner*—Khalid Masood
*Attorney, Agent, or Firm*—J. Mark Hand; Jack L. Tribble

[57] ABSTRACT

DNA encoding glutamate and avermectin–sensitive chloride channels have been cloned and characterized. The protein is capable of forming channels selectively opened with either avermectin or glutamate. The cDNA has been expressed in recombinant host cells which produce active recombinant protein. The recombinant protein is also purified from the recombinant host cells. In addition, the recombinant host cells are utilized to establish a method for identifying modulators of the receptor activity, and receptor modulators are identified. Receptor modulators active in the method disclosed herein are useful as ectoparasiticides, antiparasitic, anthelmenthic, acaracidal and insecticide agents.

16 Claims, 6 Drawing Sheets

```
CTGGCAAATAGCAAATAGAGCAAGACAAACAGCAGCAGCAACAGCAACA
ACAAGCGCCTGTGTGTCCGTGTCCCCGTGTGTGTGTGTGAGAGAGC
GAGAGCGCGCGCGTGTGTGTGTGAGTGTTTTGTACATGTGCCAGTGTG
AGTGCGTGTCACATATCAGCAGAAGAAAAACCAGCAGCAGCAGCACTAG
AAGCAGAAGCAGCAGCAGCAGTGGAAAAGCGCGCAGCCAAGCAGGAAA
ATTTGTAAACCAAGTCGGCAGAGCAGAGACATCGCAGGAGCAGCGCAGC
AGCAGCGACGCCAGCAGAAGGTCGCATCGCCCACCACAGGAGGCTGCCA
CGCCCCACGCCCCCTCTCCAGGAAGCAGGACGCACGGCACACCACACCCC
CATTCCCAACATGGGCAGCGGACACTATTTCTGGGCGATCTTATACTTTGC
CAGCCTGTGCAGTGCTTCACTAGCAAATAATGCCAAGGTAAATTTCCGAG
AAAAGGAGAAAAAAGTCTTAGATCAAATTTTAGGTGCAGGCAAATACGA
CGCCCGAATACGACCATCTGGAATAAATGGCACAGATGGTCCCGCCATAG
TCAGAATCAATCTATTCGTTCGCAGTATTATGACGATTAGTGATATTAAAA
TGGAGTACAGTGTGCAGTTAACCTTCCGTGAACAGTGGACGGATGAACGC
CTCAAGTTCGACGATATCCAGGGTCGCCTAAAGTATCTGACCCTGACGGA
GGCGAACCGCGTGTGGATGCCCGATCTTTTCTTCTCGAACGAGAAGGAGG
GACACTTCCACAACATCATCATGCCCAATGTGTATATTCGCATCTTCCCCA
ACGGATCTGTGCTATATAGTATACGTATCTCGCTGACATTGGCCTGCCCAA
TGAACCTAAAGCTGTATCCGCTGGATAGACAGATCTGCTCACTACGGATG
GCCAGCTATGGCTGGACCACCAACGACTTGGTCTTCCTGTGGAAGGAGGG
CGATCCCGTACAGGTGGTAAAGAACTTACACCTACCTCGCTTCACACTGG
AGAAGTTTCTGACTGATTACTGTAACAGTAAAACCAACACCGGTGAATAC
AGTTGCCTCAAAGTCGATCTACTATTCAGGCGAGAATTCTCATATTACTTA
ATACAAATTTATATACCATGCTGTATGTTGGTCATTGTATCATGGGTATCA
TTCTGGCTGGATCAAGGAGCAGTACCGGCGCGAGTGTCACTGGGTGTCAC
CACCCTGCTGACCATGGCCACCCAGACGTCGGGCATAAACGCCTCCCTGC
CGCCCGTTTCCTATACGAAGGCCATCGATGTGTGGACAGGCGTGTGTCTG
ACGTTCGTGTTCGGGGCCCTGCTCGAGTTCGCCCTGGTGAACTATGCATCC
CGATCAGGTTCGAATAAAGCTAACATGCATAAGGAGAATATGAAAAAGA
AGCGCCGCGATCTGGAGCAGGCCAGTTTAGATGCCGCTTCAGATCTGCTA
GATACAGATAGCAATGCAACGTTCGCAATGAAACCGTTAGTACGCCATCC
GGGCGATCCGCTGGCCCTGGAAAAGCGGCTCCAATGCGAGGTGCACATGC
AGGCCCCGAAGCGACCAAACTGCTGCAAGACCTGGCTGTCCAAGTTCCCC
ACAAGACAATGTTCTAGATCCAAGAGAATCGATGTTATATCGCGGATCAC
CTTCCCGCTGGTCTTCGCCCTGTTCAACCTGGTCTACTGGAGCACATATCT
CTTCAGGGAGGAGGAGGATGAGTAAATGCCGTTACCTATTGCCAAACACC
AATTACTTTATAGAAGGGTTGGCGCTATTGGCCAACACGAATGTACTAAC
CTATTTCTTTCATTCTTTTCCATTTCGGTTGTCTTCATTTCATGCTTTGTGTT
GCTTATGGCTTTGTTGGCTTCATTTCCGATTTGGTTGATTTCTTGATTGACA
CCTTGATTGAATGGTTCAAACCACTAAAGGACCTTCTAAGGCGCGTCTCT
GAAATGCGGTGGCTATGTAGAATCTAATACGAAATTAACTAATTATACCG
AGGGATACGTTGCGATATCGCTGTATGCTACCGGCTATGTGCCGCATGCT
ACATTTATGGTTATGTCTCGGAACAGTGCAGATAAGTTAAGAACGGTATC
CGGCAAGGCTCCATGGCACTTCCACTAAACAAATAAAGAATAATGTTTTA
TGAATGACGAAATTCTAGTTAATTGTAAGTTAAATTGATCAAGAGTGACT
GCATAGTAGATAATGTTATGAATAATTATACTAAACTATACACAAACTGA
CACACACCGCAACACTTGTTTGACTTGATTTGTTTAGAGGATGCTCCAAAT
TGTTACAAATTGATTAATTATTTTAGCTGGTTATCGACGATAACCGAGTTT
```

FIG. 1A

```
TGTTCCGGACTCTAGATTAGTTCTAAACGAAATTGCAATTGATTTGTACTT
AAATGCGTTAAGTTAGATAAGCCGCAAACAGCGAGAGGAGGTCGTAGAG
AATTCGACTTTTGTAAATATGTCATACAATAAGTTTTAAGCGAACTAGTTT
ATATGAATTCTAATTGTAAAAATCGTGTAGATAAATTTAAGTTTAGTCGAT
AAACAAACCACTAACCGAAGCGAGATACCTAGGTAAAATCAATTTAATTA
TGTTCACCATCGAAGCAAAATAAAAATCGAATCGAAAATATCAAAGAATC
CTTCAAAACACACAGAATCAAATACAGAACTTTCTTTTTGCATTTTTTGCC
CAAACTACTCTTAAATGATAAGTTCAACTGAAACTGGTGGGTATCTGCAA
GGTATTTTTACCCAAACTTTATTAGAAACTTTCTTCATTATTTATATACATA
CGGCTTGCTTTTCGTTTTAGAGTTGAATTTTTATAGTAGTTGAATTGTTCTG
GTACTCACGGGAAGTAAAACCCTCGAATTCCGATTACTTTTTCATTTGAAT
TCTTAGAATATTATAATAAATTTACATTTACCTAATTATGTATTGGGCCCA
AGTGCCGCTTAGCTAGTTAATTTCCTTAATTAGAGTTACAATATAAAAATA
TACAACATGCAAACCATAAACCAATTAACAGACAATACAAAATATTTTAT
CATGTAGTCAAAGTCCCTAAACAACTTAATGGATACTACACATAAATTGA
TTAAAATCAGTATTATAAGACAAAAATAAGATCAAGATATATACGGTTCT
TTTTATATCCAAAAATATCTTTGGTTATTTAAGTGCCTTTTGTATGCCAAG
GAGATTTCTCCCCACTTTCTTCCCTTCTCTAACTCTCTCTCTCTCTCTCTC
TTCCTAACTTTTGAATGACTCCGATCCTTTCACGCTAATATCCTTTCCTAAA
CTCAATTAGAGAAATGCACTAACCGACACCATAAACTATGCAGCTCTAAT
TTTAGAATTATAACTAAAGTGAATTCTACATAGCAACAACAGAAACAGAA
TCAGTTCCAGAACCACAATAACCAACTAACAGATAAATCGAATAAAATAT
TTCCGTAGTTTTTTAATATTTTTATTAACTTTAGCCTGTTTTATTCACATGT
TTTCTTAAACTTTTTCTTTGATTTTGGAAATGCCTTTCGTTTGCTATCATTT
ATAATCTAAAGGTAAGAAACTAAACGTAAAAGGAAATCAAAAATCAATT
GAAACTTATTCTAATATATAGACACTACACAAGGCACCCTGCATAATAAT
TGTTGTCATTAAACAAGCGTCATAAGTACGATCAGAACATATAGAAAAAC
CGAAAATGGAAATATTTATAGATACTTTCATGTTGTAAAAGTTGTGCCAA
GCAAAGACGAAACCAAAAACTAGTCAAAGAAAGAAAATCGAATGAAATC
GCGAATTATAACTATAACTCTAGCTATAGTTGTATTGTATATGAAGCTATT
GAACATACAGGGTTTTTAAATGTGAGCATATA (SEQ. ID. NO. 5)
```

FIG. 1B

MGSGHYFWAILYFASLCSASLANNAKVNFREKEKKVLDQILGAGKYD
ARIRPSGINGTDGPAIVRINLFVRSIMTISDIKMEYSVQLTFREQWTDERL
KFDDIQGRLKYLTLTEANRVWMPDLFFSNEKEGHFHNIIMPNVYIRIFPN
GSVLYSIRISLTLACPMNLKLYPLDRQICSLRMASYGWTTNDLVFLWKE
GDPVQVVKNLHLPRFTLEKFLTDYCNSKTNTGEYSCLKVDLLFRREFSY
YLIQIYIPCCMLVIVSWVSFWLDQGAVPARVSLGVTTLLTMATQTSGIN
ASLPPVSYTKAIDVWTGVCLTFVFGALLEFALVNYASRSGSNKANMHK
ENMKKKRRDLEQASLDAASDLLDTDSNATFAMKPLVRHPGDPLALEK
RLQCEVHMQAPKRPNCCKTWLSKFPTRQCSRSKRIDVISRITFPLVFALF
NLVYWSTYLFREEEDE (SEQ. ID. NO. 6)

FIG. 2

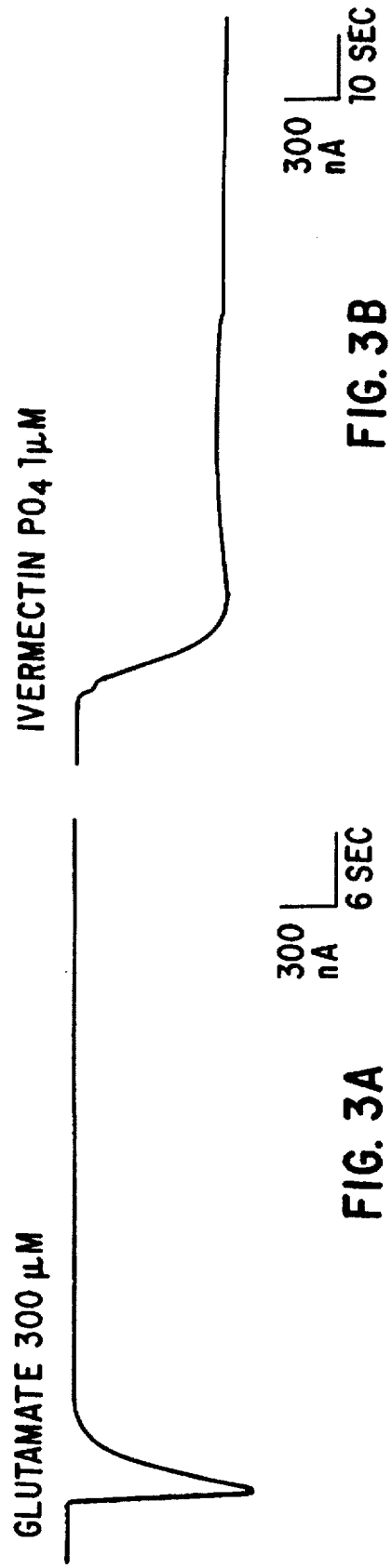
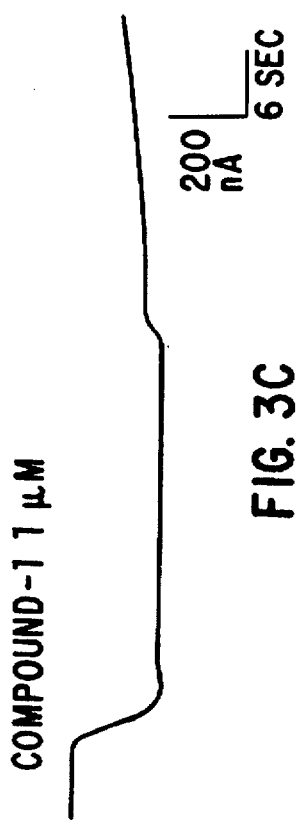
FIG. 3A  
FIG. 3B  
FIG. 3C

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TGGGTNWSNT TYTGGTT ( 2 ) INFORMATION FOR SEQ ID NO:2:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

GCNCCDATCC ANACRTCDAT                                                                                          20

(2) INFORMATION FOR SEQ ID NO:3:

(i) SEQUENCE CHARACTERISTICS:
(A) LENGTH: 50 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:3:

```
Trp Val Thr Phe Trp Leu Asp Gln Gly Ala Val Pro Ala Arg Val Ser
 1               5                  10                  15

Leu Gly Val Thr Thr Leu Leu Thr Met Ala Thr Gln Thr Ser Gly Ile
                20                  25                  30

Asn Ala Ser Leu Pro Pro Val Ser Tyr Thr Lys Ala Ile Asp Val Trp
                35              40              45

Ile Gly
    50
```

(2) INFORMATION FOR SEQ ID NO:4:

(i) SEQUENCE CHARACTERISTICS:
(A) LENGTH: 152 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

TGGGTTACTT TTTGGTTGGA TCAAGGAGCA GTACCGGCGC GAGTGTCACT GGGTGTCACC         60
ACCCTGCTGA CCATGGCCAC CCAGACGTCG GGCATAAACG CCTCCCTGCC GCCCGTTTCC        120
TATACGAAGG CCATAGACGT TTGGATCGGT GC                                      152

(2) INFORMATION FOR SEQ ID NO:5:

(i) SEQUENCE CHARACTERISTICS:
(A) LENGTH: 3958 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

CTGGCAAATA GCAAATAGAG CAAGACAAAC AGCAGCAGCA ACAGCAACAA CAAGCGCCTG         60
TGTGTCCGTG TCCCCGTGTG TGTGTGTGTG AGAGAGAGCG AGAGCGCGCG CGTGTGTGTG        120
TGTGAGTGTT TTGTACATGT GCCAGTGTGA GTGCGTGTCA CATATCAGCA GAAGAAAAAC        180
CAGCAGCAGC AGCACTAGAA GCAGAAGCAG CAGCAGCAGT GGAAAGCGC GCAGCCAAGC         240
AGGAAAATTT GTAAACCAAG TCGGCAGAGC AGAGACATCG CAGGAGCAGC GCAGCAGCAG        300

```
CGACGCCAGC AGAAGGTCGC ATCGCCCACC ACAGGAGGCT GCCACGCCCC ACGCCCCCTC    360
TCCAGGAAGC AGGACGCACG GCACACCACA CCCCCATTCC CAACATGGGC AGCGGACACT    420
ATTTCTGGGC GATCTTATAC TTTGCCAGCC TGTGCAGTGC TTCACTAGCA AATAATGCCA    480
AGGTAAATTT CCGAGAAAAG GAGAAAAAAG TCTTAGATCA AATTTTAGGT GCAGGCAAAT    540
ACGACGCCCG AATACGACCA TCTGGAATAA ATGGCACAGA TGGTCCCGCC ATAGTCAGAA    600
TCAATCTATT CGTTCGCAGT ATTATGACGA TTAGTGATAT TAAAATGGAG TACAGTGTGC    660
AGTTAACCTT CCGTGAACAG TGGACGGATG AACGCCTCAA GTTCGACGAT ATCCAGGGTC    720
GCCTAAAGTA TCTGACCCTG ACGGAGGCGA ACCGCGTGTG GATGCCCGAT CTTTCTTCT     780
CGAACGAGAA GGAGGGACAC TTCCACAACA TCATCATGCC CAATGTGTAT ATTCGCATCT    840
TCCCCAACGG ATCTGTGCTA TATAGTATAC GTATCTCGCT GACATTGGCC TGCCCAATGA    900
ACCTAAAGCT GTATCCGCTG GATAGACAGA TCTGCTCACT ACGGATGGCC AGCTATGGCT    960
GGACCACCAA CGACTTGGTC TTCCTGTGGA AGGAGGGCGA TCCCGTACAG GTGGTAAAGA   1020
ACTTACACCT ACCTCGCTTC ACACTGGAGA AGTTTCTGAC TGATTACTGT AACAGTAAAA   1080
CCAACACCGG TGAATACAGT GCCTCAAAG TCGATCTACT ATTCAGGCGA GAATTCTCAT    1140
ATTACTTAAT ACAAATTTAT ATACCATGCT GTATGTTGGT CATTGTATCA TGGGTATCAT   1200
TCTGGCTGGA TCAAGGAGCA GTACCGGCGC GAGTGTCACT GGGTGTCACC ACCTGCTGA    1260
CCATGGCCAC CCAGACGTCG GGCATAAACG CCTCCCTGCC GCCCGTTTCC TATACGAAGG   1320
CCATCGATGT GTGGACAGGC GTGTGTCTGA CGTTCGTGTT CGGGCCCTG CTCGAGTTCG    1380
CCCTGGTGAA CTATGCATCC CGATCAGGTT CGAATAAAGC TAACATGCAT AAGGAGAATA   1440
TGAAAAAGAA GCGCCGCGAT CTGGAGCAGG CCAGTTTAGA TGCCGCTTCA GATCTGCTAG   1500
ATACAGATAG CAATGCAACG TTCGCAATGA AACCGTTAGT ACGCCATCCG GGCGATCCGC   1560
TGGCCCTGGA AAAGCGGCTC CAATGCGAGG TGCACATGCA GGCCCCGAAG CGACCAAACT   1620
GCTGCAAGAC CTGGCTGTCC AAGTTCCCCA CAAGACAATG TTCTAGATCC AAGAGAATCG   1680
ATGTTATATC GCGGATCACC TTCCCGCTGG TCTTCGCCCT GTTCAACCTG GTCTACTGGA   1740
GCACATATCT CTTCAGGGAG GAGGAGGATG AGTAAATGCC GTTACCTATT GCCAAACACC   1800
AATTACTTTA TAGAAGGGTT GGCGCTATTG GCCAACACGA ATGTACTAAC CTATTTCTTT   1860
CATTCTTTTC CATTTCGGTT GTCTTCATTT CATGCTTTGT GTTGCTTATG GCTTTGTTGG   1920
CTTCATTTCC GATTTGGTTG ATTTCTTGAT TGACACCTTG ATTGAATGGT TCAAACCACT   1980
AAAGGACCTT CTAAGGCGCG TCTCTGAAAT GCGGTGGCTA TGTAGAATCT AATACGAAAT   2040
TAACTAATTA TACCGAGGGA TACGTTGCGA TATCGCTGTA TGCTACCGGC TATGTGCCGC   2100
ATGCTACATT TATGGTTATG TCTCGGAACA GTGCAGATAA GTTAAGAACG GTATCCGGCA   2160
AGGCTCCATG GCACTTCCAC TAAACAAATA AGAATAATG TTTTATGAAT GACGAAATTC    2220
TAGTTAATTG TAAGTTAAAT TGATCAAGAG TGACTGCATA GTAGATAATG TTATGAATAA   2280
TTATACTAAA CTATACACAA ACTGACACAC ACCGCAACAC TTGTTTGACT TGATTTGTTT   2340
AGAGGATGCT CCAAATTGTT ACAAATTGAT TAATTATTTT AGCTGGTTAT CGACGATAAC   2400
CGAGTTTTGT TCCGGACTCT AGATTAGTTC TAAACGAAAT TGCAATTGAT TTGTACTTAA   2460
ATGCGTTAAG TTAGATAAGC CGCAAACAGC GAGAGGAGGT CGTAGAGAAT CGACTTTTG    2520
TAAATATGTC ATACAATAAG TTTTAAGCGA ACTAGTTTAT ATGAATTCTA ATTGTAAAAA   2580
TCGTGTAGAT AAATTTAAGT TTAGTCGATA AACAAACCAC TAACCGAAGC GAGATACCTA   2640
GGTAAAATCA ATTTAATTAT GTTCACCATC GAAGCAAAAT AAAAATCGAA TCGAAAATAT   2700
```

| | | | | | |
|---|---|---|---|---|---|
| CAAAGAATCC | TTCAAAACAC | ACAGAATCAA | ATACAGAACT | TTCTTTTTGC | ATTTTTTGCC | 2760 |
| CAAACTACTC | TTAAATGATA | AGTTCAACTG | AAACTGGTGG | GTATCTGCAA | GGTATTTTA | 2820 |
| CCCAAACTTT | ATTAGAAACT | TTCTTCATTA | TTTATATACA | TACGGCTTGC | TTTTCGTTTT | 2880 |
| AGAGTTGAAT | TTTTATAGTA | GTTGAATTGT | TCTGGTACTC | ACGGGAAGTA | AAACCCTCGA | 2940 |
| ATTCCGATTA | CTTTTTCATT | TGAATTCTTA | GAATATTATA | ATAAATTTAC | ATTTACCTAA | 3000 |
| TTATGTATTG | GGCCCAAGTG | CCGCTTAGCT | AGTTAATTTC | CTTAATTAGA | GTTACAATAT | 3060 |
| AAAAATATAC | AACATGCAAA | CCATAAACCA | ATTAACAGAC | AATACAAAAT | ATTTTATCAT | 3120 |
| GTAGTCAAAG | TCCCTAAACA | ACTTAATGGA | TACTACACAT | AAATTGATTA | AAATCAGTAT | 3180 |
| TATAAGACAA | AAATAAGATC | AAGATATATA | CGGTTCTTTT | TATATCCAAA | AATATCTTTG | 3240 |
| GTTATTTAAG | TGCCTTTTGT | ATGCCAAGGA | GATTTCTCCC | CACTTTCTTC | CCTTCTCTAA | 3300 |
| CTCTCTCTCT | CTCTCTCTCT | CTTCCTAACT | TTTGAATGAC | TCCGATCCTT | TCACGCTAAT | 3360 |
| ATCCTTTCCT | AAACTCAATT | AGAGAAATGC | ACTAACCGAC | ACCATAAACT | ATGCAGCTCT | 3420 |
| AATTTTAGAA | TTATAACTAA | AGTGAATTCT | ACATAGCAAC | AACAGAAACA | GAATCAGTTC | 3480 |
| CAGAACCACA | ATAACCAACT | AACAGATAAA | TCGAATAAAA | TATTTCCGTA | GTTTTTTAAT | 3540 |
| ATTTTTATTA | ACTTTAGCCT | GTTTTATTCA | CATGTTTCT | TAAACTTTTT | CTTTGATTTT | 3600 |
| GGAAATGCCT | TTCGTTTGCT | ATCATTTATA | ATCTAAAGGT | AAGAAACTAA | ACGTAAAAGG | 3660 |
| AAATCAAAAA | TCAATTGAAA | CTTATTCTAA | TATATAGACA | CTACACAAGG | CACCCTGCAT | 3720 |
| AATAATTGTT | GTCATTAAAC | AAGCGTCATA | AGTACGATCA | GAACATATAG | AAAAACCGAA | 3780 |
| AATGGAAATA | TTTATAGATA | CTTTCATGTT | GTAAAAGTTG | TGCCAAGCAA | AGACGAAACC | 3840 |
| AAAAACTAGT | CAAAGAAAGA | AAATCGAATG | AAATCGCGAA | TTATAACTAT | AACTCTAGCT | 3900 |
| ATAGTTGTAT | TGTATATGAA | GCTATTGAAC | ATACAGGGTT | TTTAAATGTG | AGCATATA | 3958 |

( 2 ) INFORMATION FOR SEQ ID NO:6:

( i ) SEQUENCE CHARACTERISTICS:
( A ) LENGTH: 456 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:6:

```
Met Gly Ser Gly His Tyr Phe Trp Ala Ile Leu Tyr Phe Ala Ser Leu
 1               5                  10                  15

Cys Ser Ala Ser Leu Ala Asn Asn Ala Lys Val Asn Phe Arg Glu Lys
            20                  25                  30

Glu Lys Lys Val Leu Asp Gln Ile Leu Gly Ala Gly Lys Tyr Asp Ala
        35                  40                  45

Arg Ile Arg Pro Ser Gly Ile Asn Gly Thr Asp Gly Pro Ala Ile Val
    50                  55                  60

Arg Ile Asn Leu Phe Val Arg Ser Ile Met Thr Ile Ser Asp Ile Lys
65                  70                  75                  80

Met Glu Tyr Ser Val Gln Leu Thr Phe Arg Glu Gln Trp Thr Asp Glu
                85                  90                  95

Arg Leu Lys Phe Asp Asp Ile Gln Gly Arg Leu Lys Tyr Leu Thr Leu
            100                 105                 110

Thr Glu Ala Asn Arg Val Trp Met Pro Asp Leu Phe Phe Ser Asn Glu
        115                 120                 125

Lys Glu Gly His Phe His Asn Ile Ile Met Pro Asn Val Tyr Ile Arg
```

|   |   |   |   |   | 130 |   |   |   |   |   | 135 |   |   |   |   |   | 140 |   |   |
|---|---|---|---|---|---|---|---|---|---|---|---|---|---|---|---|---|---|---|---|
| Ile 145 | Phe | Pro | Asn | Gly | Ser 150 | Val | Leu | Tyr | Ser | Ile 155 | Arg | Ile | Ser | Leu | Thr 160 |
| Leu | Ala | Cys | Pro | Met 165 | Asn | Leu | Lys | Leu | Tyr 170 | Pro | Leu | Asp | Arg | Gln 175 | Ile |
| Cys | Ser | Leu | Arg 180 | Met | Ala | Ser | Tyr | Gly 185 | Trp | Thr | Thr | Asn | Asp 190 | Leu | Val |
| Phe | Leu | Trp 195 | Lys | Glu | Gly | Asp | Pro 200 | Val | Gln | Val | Val | Lys 205 | Asn | Leu | His |
| Leu | Pro 210 | Arg | Phe | Thr | Leu | Glu 215 | Lys | Phe | Leu | Thr | Asp 220 | Tyr | Cys | Asn | Ser |
| Lys 225 | Thr | Asn | Thr | Gly | Glu 230 | Tyr | Ser | Cys | Leu | Lys 235 | Val | Asp | Leu | Leu | Phe 240 |
| Arg | Arg | Glu | Phe | Ser 245 | Tyr | Tyr | Leu | Ile | Gln 250 | Ile | Tyr | Ile | Pro | Cys 255 | Cys |
| Met | Leu | Val | Ile 260 | Val | Ser | Trp | Val | Ser 265 | Phe | Trp | Leu | Asp | Gln 270 | Gly | Ala |
| Val | Pro | Ala 275 | Arg | Val | Ser | Leu | Gly 280 | Val | Thr | Thr | Leu | Leu 285 | Thr | Met | Ala |
| Thr | Gln 290 | Thr | Ser | Gly | Ile | Asn 295 | Ala | Ser | Leu | Pro | Pro 300 | Val | Ser | Tyr | Thr |
| Lys 305 | Ala | Ile | Asp | Val | Trp 310 | Thr | Gly | Val | Cys | Leu 315 | Thr | Phe | Val | Phe | Gly 320 |
| Ala | Leu | Leu | Glu | Phe 325 | Ala | Leu | Val | Asn | Tyr 330 | Ala | Ser | Arg | Ser | Gly 335 | Ser |
| Asn | Lys | Ala | Asn 340 | Met | His | Lys | Glu | Asn 345 | Met | Lys | Lys | Arg 350 | Arg | Asp |
| Leu | Glu | Gln 355 | Ala | Ser | Leu | Asp | Ala 360 | Ala | Ser | Asp | Leu | Leu 365 | Asp | Thr | Asp |
| Ser | Asn 370 | Ala | Thr | Phe | Ala | Met 375 | Lys | Pro | Leu | Val | Arg 380 | His | Pro | Gly | Asp |
| Pro 385 | Leu | Ala | Leu | Glu | Lys 390 | Arg | Leu | Gln | Cys | Glu 395 | Val | His | Met | Gln | Ala 400 |
| Pro | Lys | Arg | Pro | Asn 405 | Cys | Cys | Lys | Thr | Trp 410 | Leu | Ser | Lys | Phe | Pro 415 | Thr |
| Arg | Gln | Cys | Ser 420 | Arg | Ser | Lys | Arg | Ile 425 | Asp | Val | Ile | Ser | Arg 430 | Ile | Thr |
| Phe | Pro | Leu 435 | Val | Phe | Ala | Leu | Phe 440 | Asn | Leu | Val | Tyr | Trp 445 | Ser | Thr | Tyr |
| Leu | Phe 450 | Arg | Glu | Glu | Glu | Asp 455 | Glu |

DNA ENCODING GLUTAMATE GATED CHLORIDE CHANNELS

BACKGROUND OF THE INVENTION

Glutamate-gated chloride channels, or H-receptors, have been identified in anhropod nerve and muscle [Lingle, C. & Marder, E. *Brain Res.* 212, 481–488 (1981)], [Horseman, B. G., Seymour, C., Bermudez, I. & Beadle, D. J. *Neurosci. Lett.* 85, 65–70 (1988)], [Wafford, K. A. & Sattelle, D. B. *J. Exp. Bio.* 144, 449–462 (1989)], [Lea, T. J. & Usherwood, P. N. R. *Comp. Gen. Parmacol.* 4, 333–350 (1973)], [Cull-Candy, S. G. *J. Physiol.* 255, 449–464 (1976)], and cloned from the soil nematode *Caenorhabditis elegans* [Cully, D. F., Vassilatis, D. K., Liu, K. K., Paress, P. S., Van der Ploeg, L. H. T., Schaeffer, J. M. & Arena, J. P. *Nature* 371, 707–711 (1994)]. They are important targets for the widely used avermectin class of anthelmintic and insecticidal compounds. The avermectins are a family of macrocyclic lactones originally isolated from the actinomycete *Streptomyces avermitilis*. The semisynthetic avermectin derivative, ivermectin (22,23-dihydroavermectin $B_{1a}$), is used throughout the world to treat parasitic helminths and insect pests of man and animals. Discovered some 15 years ago, the avermectins remain the most potent broad spectrum endectocides exhibiting low toxicity to the host. Avermectins exhibit an essentially irreversible interaction with a high affinity site in nematode [Schaeffer, J. M. & Haines, H. W. *Biochem. Pharm.* 38, 2329–2338 (1989); Cully, D. F. & Paress P. S., *Molecular Pharm.* 40:326–332 (1991)] and insect [Rohrer, S. P., Meinke, P. T., Hayes, E. C., Mrozik, H. & Schaeffer, J. M. *Proc. Natl. Acad. Sci,* 89, 4168–4172 (1992)] membranes and induce an increase in membrane chloride permeability in nematodes [Martin, R. J. & Pennington, A. J. Br. *J. Pharmacol.* 98, 747–756 (1989)], arthropods [Scott, R. H. & Duce, I. R. *Pestic. Sci.* 16, 599–604 (1985)], [Duce, I. R. & Scott, R. H. Brit. *J. Pharmacol.* 85, 395–401 (1985)] and crustaceans [Zufall, F., Franke, C. & Hatt, H. *J. Exp. Biol.* 142, 191–205 (1989)]. Avermectins have been shown to directly activate glutamate-gated chloride channels from *C. elegans* [Arena, J. P., Liu, K. K., Paress, P. S. & Cully, D. F. *Mol. Pharmacol.* 40, 368–374 (1991); Arena, J. P., Liu, K. K., Paress, P. S., Schaeffer, J. M. & Cully, D. F. *Mol. Brain Res.* 15, 339–348 (1992); Cully, D. F., Vassilatis, D. K., Liu, K. K., Paress, P. S., Van der Ploeg, L. H. T., Schaeffer, J. M. & Arena, J. P. *Nature* 371, 707–711 (1994)], and to directly activate or potentiate glutamate-gated chloride channel current in locust muscle [Scott, R. H. & Duce, I. R. *Pestic, Sci.* 16, 599–604 (1985); Aydar, E., Harding, L., Beadle, D. J. & Bermudez, I. Proceedings of the British Pharmacological Society p24 (1993)].

SUMMARY OF THE INVENTION

A target of avermectin action in arthropods has been cloned and characterized and it represents a new member of the glutamate-gated chloride channel class of ligand-gated channels. Using a reverse transcription PCR approach a functional DNA molecule encoding the Drosophila glutamate-, and avermectin-sensitive chloride channel has been isolated. The electrophysiological and structural properties of the protein is disclosed, as is the amino acid and nucleotide sequence. The recombinant protein is useful to identify modulators of the channel. Modulators identified in this process are useful as therapeutic agents, including insecticides, ectoparasiticides, endoparasiticides, acaracides and anthelminthics.

BRIEF DESCRIPTION OF THE DRAWING

FIG. 1 The nucleotide sequence of Dros GluCl is shown.

FIG. 2 The amino acid sequence of Dros GluCl is shown.

FIG. 3 Electrophysiological properties Dros GluCl expressed in Xenopus oocytes is shown.

DETAILED DESCRIPTION

Figure 4:
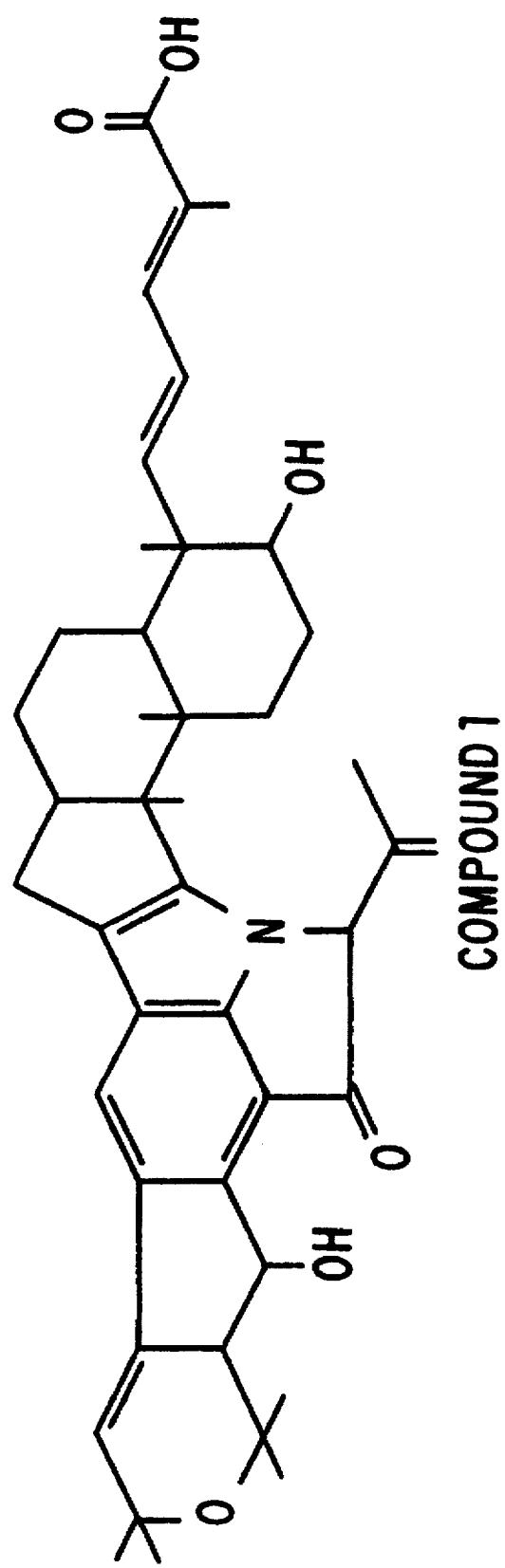
FIG. 4 Structure of Compound-1 is shown.

The present invention relates to DNA encoding an arthropod glutamate- and avermectin-sensitive chloride channel (GluCl) which was isolated from GluCl producing cells. GluCl, as used herein, refers to protein which can specifically function as an anion channel gated by glutamate or avermectin.

The amino acid sequence of the Dros GluCl was not previously known, nor was the nucleotide sequence encoding Dros GluCl known. This is the first reported cloning of a glutamate-gated chloride channel from arthropods. Dros GluCl is related to the previously cloned *C. elegans* GluClα and GluClβ [Cully, D. F., Vassilatis, D. K., Liu, K. K., Paress, P. S., Van der Ploeg, L. H. T., Schaeffer, J. M. & Arena, J. P. supra]. Unlike the *C. elegans* channel Dros GluCl requires only a single polypeptide for direct activation with avermectin or glutamate. In addition, Dros GluCl is directly activated by the insectidal agent, Compound-1 (FIG. 5) which is the subject of U.S. Pat. No. 5,399,582 and is fully described therein. It is predicted that all Drosophila-related organisms sensitive to the avermectins will contain the described glutamate and avermectin-sensitive channels. Drosophila cells capable of producing GluCl include, but are not limited to muscle or nerve cells isolated from organisms that show sensitivity to the avermectins. Avermectin sensitive animals are diverse and include invertebrates belonging to the phyla Anhropoda and Nematoda.

Other cells and cell lines may also be suitable for use to isolate GluCl cDNA. Selection of suitable cells may be done by screening for GluCl activity in cell extracts. GluCl activity can be monitored by performing a radiolabeled-ivermectin or radiolabeled Compound-1, or derivative thereof, binding assay (Cully and Paress, supra; Rohrer et al, supra) or by direct electrophysiological measurment of a glutamate-, Compound-1 or avermectin-sensitive chloride channel [Martin, R. J. & Pennington, A. J. Br. *J. Pharmacol.* 98, 747–756 (1989); Scott, R. H. & Duce, I. R. *Pestic. Sci.* 16, 599–604 (1985); Duce, I. R. & Scott, R. H. Brit. *J. Pharmacol.* 85, 395–401 (1985); Zufall, F., Franke, C. & Hatt, H. *J. Exp. Biol.* 142, 191–205 (1989)]. Cells which possess GluCl activity in this assay may be suitable for the isolation of GluCl DNA or RNA.

Any of a variety of procedures known in the an may be used to molecularly clone GluCl DNA. These methods include, but are not limited to, direct functional expression of the GluCl genes following the construction of a GluCl-containing DNA library in an appropriate expression vector system. Another method is to screen GluCl-containing DNA library constructed in a bacteriophage or plasmid shuttle vector with a labelled oligonucleotide probe designed from the amino acid sequence of the GluCl protein. An additional method consists of screening a GluCl-containing DNA library constructed in a bacteriophage or plasmid shuttle vector with a partial cDNA encoding the GluCl protein. This partial cDNA is obtained by the specific PCR amplification of GluCl DNA fragments through the design of degenerate oligonucleotide primers from the amino acid sequence of the purified GluCl proteins.

Another method is to isolate RNA from GluCl-producing cells and translate the RNA into protein via an in vitro or an in vivo translation system. The translation of the RNA into a peptide or a protein will result in the production of at least a portion of the GluCl protein which can be identified by, for example, immunological reactivity with an anti-GluCl antibody or by biological activity of GluCl protein. In this method, pools of RNA isolated from GluCl-producing cells are analyzed for the presence of an RNA which encodes at least a portion of the GluCl protein. Further fractionation of the RNA pool can be done to purify the GluCl RNA from non-GluCl RNA. The peptide or protein produced by this method may be analyzed to provide amino acid sequences which in turn are used to provide primers for production of GluCl cDNA, or the RNA used for translation can be analyzed to provide nucleotide sequences encoding GluCl and produce probes for this production of GluCl cDNA. This method is known in the art and can be found in, for example, Sambrook, J., Fritsch, E. F., Maniatis, T. in Molecular Cloning: A Laboratory Manual, Second Edition, Cold Spring Harbor Laboratory Press, Cold Spring Harbor, N.Y. 1989.

It is readily apparent to those skilled in the art that other types of libraries, as well as libraries constructed from other cells or cell types, may be useful for isolating GluCl-encoding DNA. Other types of libraries include, but are not limited to, cDNA libraries derived from other cells, and genomic DNA libraries that include YAC (yeast artificial chromosome) and cosmid libraries.

It is readily apparent to those skilled in the art that suitable cDNA libraries may be prepared from cells or cell lines which have GluCl activity. The selection of cells or cell lines for use in preparing a cDNA library to isolate GluCl cDNA may be done by first measuring cell associated GluCl activity using the electrophysiological measurment of avermectin and glutamate-sensitive chloride channels or a glutamate or avermectin ligand binding assay.

Preparation of cDNA libraries can be performed by standard techniques well known in the art. Well known cDNA library construction techniques can be found for example, in Sambrook, J., Fritsch, E. F., Maniatis, T. in Molecular Cloning: A Laboratory Manual, Second Edition, Cold Spring Harbor Laboratory Press, Cold Spring Harbor, N.Y. 1989.

It is also readily apparent to those skilled in the art that DNA encoding GluCl may also be isolated from a suitable genomic DNA library. Construction of genomic DNA libraries can be performed by standard techniques well known in the art. Well known genomic DNA library construction techiques can be found in Sambrook, J., Fritsch, E. F., Maniatis, T. in Molecular Cloning: A Laboratory Manual, Second Edition, Cold Spring Harbor Laboratory Press, Cold Spring Harbor, N.Y. 1989.

In order to clone the GluCl gene by the above methods, the amino acid sequence of GluCl may be necessary. To accomplish this, GluCl protein may be purified and partial amino acid sequence determined by automated sequenators. It is not necessary to determine the entire amino acid sequence, but the linear sequence of two regions of 6 to 8 amino acids from the protein is determined for the production of primers for PCR amplification of a partial GluCl DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the GluCl sequence but will be capable of hybridizing to GluCl DNA even in the presence of DNA oligonucleotides with mismatches. The mismatched DNA oligonucleotides may still sufficiently hybridize to the GluCl DNA to permit identification and isolation of GluCl encoding DNA. DNA isolated by these methods can be used to screen DNA libraries from a variety of cell types, from invertebrate and vertebrate sources, and to isolate homologous genes.

Purified biologically active GluCl may have several different physical forms. GluCl may exist as a full-length nascent or unprocessed polypeptide, or as partially processed polypeptides or combinations of processed polypeptides. The full-length nascent GluCl polypeptide may be postranslationally modified by specific proteolytic cleavage events which result in the formation of fragments of the full length nascent polypeptide. A fragment, or physical association of fragments may have the full biological activity associated with GluCl (glutamate-, avermectin- or Compound-1 sensitive channel). However, the degree of GluCl activity may vary between individual GluCl fragments and physically associated GluCl polypeptide fragments.

The cloned GluCl DNA obtained through the methods described herein may be recombinantly expressed by molecular cloning into an expression vector containing a suitable promoter and other appropriate transcription regulatory elements, and transferred into prokaryotic or eukaryotic host cells to produce recombinant GluCl. Techniques for such manipulations are fully described in Sambrook, J., et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including E. coli, bluegreen algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically as designed plasmids or viruses.

A variety of mammalian expression vectors may be used to express recombinant GluCl in mammalian cells. Commercially available mammalian expression vectors which may be suitable for recombinant GluCl expression, include but are not limited to, pMAMneo (Clontech), pcDNA3 (Invitrogen), pMC1neo (Stratagene), pXT1 (Stratagene), pSG5 (Stratagene), EBO-pSV2-neo (ATCC 37593) pBPV-1(8–2) (ATCC 37110), pdBPV-MMTneo(342–12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

A variety of bacterial expression vectors may be used to express recombinant GluCl in bacterial cells. Commercially available bacterial expression vectors which may be suitable for recombinant GluCl expression include, but are not limited to pET vectors (Novagen) and pQE vectors (Qiagen).

A variety of fungal cell expression vectors may be used to express recombinant GluCl in fungal cells such as yeast. Commerically available fungal cell expression vectors which may be suitable for recombinant GluCl expression include but are not limited to pYES2 (Invitrogen) and Pichia expression vectors (Invitrogen).

A variety of insect cell expression vectors may be used to express recombinant GluCl in insect cells. Commercially available insect cell expression vectors which may be suitable for recombinant expression of GluCl include but are not limited to pBlueBacII (Invitrogen).

DNA encoding GluCl may also be cloned into an expression vector for expression in a recombinant host cell. Recombinant host cells may be prokaryotic or eukaryotic, including but not limited to bacteria such as E. coil, fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including but not limited to transformation, transfection, protoplast fusion, lipofection, and electroporation. The expression vector-containing cells are clonally propagated and individually analyzed to determine whether they produce GluCl protein. Identification of GluCl expressing host cell clones may be done by several means, including but not limited to immunological reactivity with anti-GluCl antibodies, and the presence of host cell-associated GluCl activity.

Expression of GluCl DNA may also be performed using in vitro produced synthetic mRNA. Synthetic mRNA or mRNA isolated from GluCl producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the GluCl DNA sequence(s) that yields optimal levels of GluCl activity and/or GluCl protein, GluCl DNA molecules including, but not limited to, the following can be constructed: the full-length open reading frame of the GluCl cDNA encoding the GluCl protein (corresponding to the first nucleotide of the first methionine and the last nucleotide before the first stop codon) and constructs containing portions of the cDNA encoding GluCl protein. All constructs can be designed to contain none, all or portions of the 5' or the 3' untranslated region of GluCl cDNA. GluCl activity and levels of protein expression can be determined following the introduction, both singly and in combination, of these constructs into appropriate host cells. Following determination of the GluCl DNA cassette yielding optimal expression in transient assays, this GluCl DNA construct is transferred to a variety of expression vectors, for expression in host cells including, but not limited to, mammalian cells, baculovirus-infected insect cells, *E. coli*, and the yeast *S. cerevisiae*.

Host cell transfectants and microinjected oocytes may be assayed for both the levels of GluCl channel activity and levels of GluCl protein by the following methods. In the case of recombinant host cells, this involves the co-transfection of one or possibly two or more plasmids, containing the GluCl DNA. In the case of oocytes, this involves the injection of synthetic RNAs or DNAs for one or more GluCl proteins. Following an appropriate period of time to allow for expression, cellular protein is metabolically labelled with for example $^{35}S$-methionine for 24 hours, after which cell lysates and cell culture supernatants are harvested and subjected to immunprecipitation with polyclonal antibodies directed against the GluCl protein.

Other methods for detecting GluCl activity involve the direct measurement of GluCl activity in whole cells transfected with GluCl cDNA or oocytes injected with GluCl mRNA. GluCl activity is measured by specific ligand binding and electrophysiological characteristics of the host cells expressing GluCl DNA. In the case of recombinant host cells expressing GluCl patch voltage clamp techniques can be used to measure chloride channel activity and quantitate GluCl protein. In the case of oocytes patch clamp as well as two electrode voltage clamp techniques can be used to measure chloride channel activity and quantitate GluCl protein.

Levels of GluCl protein in host cells are quantitated by immunoaffinity and/or ligand affinity techniques. Cells expressing GluCl can be assayed for the number of GluCl molecules expressed by measuring the amount of radioactive glutamate or ivermectin binding to cell membranes. GluCl-specific affinity beads or GluCl-specific antibodies are used to isolate for example $^{35}S$-methionine labelled or unlabelled GluCl protein. Labelled GluCl protein is analyzed by SDS-PAGE. Unlabelled GluCl protein is detected by Western blotting, ELISA or RIA assays employing GluCl specific antibodies.

Because the genetic code is degenerate, more than one codon may be used to encode a particular amino acid, and therefore, the amino acid sequence can be encoded by any of a set of similar DNA oligonucleotides. Only one member of the set will be identical to the GluCl sequence but will be capable of hybridizing to GluCl DNA even in the presence of DNA oligonucleotides with mismatches under appropriate conditions. Under alternate conditions, the mismatched DNA oligonucleotides may still hybridize to the GluCl DNA to permit identification and isolation of GluCl encoding DNA.

DNA encoding GluCl from a particular organism may be used to isolate and purify homologues of GluCl from other organisms. To accomplish this, the first GluCl DNA may be mixed with a sample containing DNA encoding homologues of GluCl under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alternative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis. Examples of altered properties include but are not limited to changes in the affinity of an enzyme for a substrate or a receptor for a ligand.

As used herein, a "functional derivative" of GluCl is a compound that possesses a biological activity (either functional or structural) that is substantially similar to the biological activity of GluCl. The term "functional derivatives" is intended to include the "fragments," "variants," "degenerate variants," "analogs" and "homologues" or to "chemical derivatives" of GluCl. The term "fragment" is meant to refer to any polypeptide subset of GluCl. The term "variant" is meant to refer to a molecule substantially similar in structure and function to either the entire GluCl molecule or to a fragment thereof. A molecule is "substantially similar" to GluCl if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire GluCl molecule or to a fragment thereof.

Following expression of GluCl in a recombinant host cell, GluCl protein may be recovered to provide GluCl in active form. Several GluCl purification procedures are available and suitable for use. As described above for purification of GluCl from natural sources, recombinant GluCl may be purified from cell lysates and extracts, or from conditioned culture medium, by various combinations of, or individual application of salt fractionation, ion exchange chromatography, size exclusion chromatography, hydroxylapatite adsorption chromatography and hydrophobic interaction chromatography.

In addition, recombinant GluCl can be separated from other cellular proteins by use of an immunoaffinity column made with monoclonal or polyclonal antibodies specific for full length nascent GluCl, polypeptide fragments of GluCl or GluCl proteins.

Monospecific antibodies to GluCl are purified from mammalian antisera containing antibodies reactive against GluCl or are prepared as monoclonal antibodies reactive with GluCl using the technique of Kohler and Milstein, *Nature* 256: 495–497 (1975). Monospecific antibody as used herein is defined as a single antibody species or multiple antibody species with homogenous binding characteristics for GluCl. Homogenous binding as used herein refers to the ability of the antibody species to bind to a specific antigen or epitope, such as those associated with the GluCl, as described above. GluCl specific antibodies are raised by immunizing animals such as mice, rats, guinea pigs, rabbits, goats, horses and the like, with rabbits being preferred, with an appropriate concentration of GluCl either with or without an immune adjuvant.

Preimmune serum is collected prior to the first immunization. Each animal receives between about 0.1 mg and about 1000 mg of GluCl associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of GluCl in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with GluCl are prepared by immunizing inbred mice, preferably Balb/c, with GluCl. The mice are immunized by the IP or SC route with about 0.1 mg to about 10 mg, preferably about 1 mg, of GluCl in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of GluCl in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using GluCl as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristane primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-GluCl mAb is carried out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of GluCl in body fluids or tissue and cell extracts.

It is readily apparent to those skilled in the art that the above described methods for producing monospecific antibodies may be utilized to produce antibodies specific for GluCl polypeptide fragments, or full-length nascent GluCl polypeptide. Specifically, it is readily apparent to those skilled in the art that monospecific antibodies may be generated which are specific for only one GluCl protein or the fully functional glutamate-, Compound-1 and avermectin-sensitive chloride channel.

GluCl antibody affinity columns are made by adding the antibodies to Affigel-10 (Biorad), a gel support which is activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) and the cell culture supernatants or cell extracts containing GluCl or GluCl protein fragments are slowly passed through the column. The column is then washed with phosphate buffered saline until the optical density ($A_{280}$) falls to background, then the protein is eluted with 0.23M glycine-HCl (pH 2.6). The purified GluCl protein is then dialyzed against phosphate buffered saline.

DNA clones, termed pGluCl, are identified which encode proteins that, when expressed in Xenopus oocytes as homomeric channels, or as heteromeric channels with other members of the GluCl family, are directly activated with glutamate, or avermectin. Glutamate-gated chloride channels have only been reported in invertebrates and are found on insect muscle and neuronal somata, crustacean muscle, and express in oocytes from insect muscle poly $(A)^+$ RNA [Lingle, C. & Marder, E. Brain Res. 212, 481–488 (1981)], [Horseman, B. G., Seymour, C., Bermudez, I. & Beadle, D. J. Neurosci. Lett. 85, 65–70 (1988)], [Wafford, K. A., & Sattelle, D. B. J. Exp. Biol. 144, 449–462 (1989)], [Lea, T. J. & Usherwood, P. N. R. Comp. Gen. Pharmacol. 4, 333–350 (1973)], [Cull-Candy, S. G. J. Physiol. 255, 449–464 (1976)]. [Fraser, S. P., et al., Mol. Brain Res. 8, 331–341 (1990)] and have been cloned from the soil nematode C. elegans [Cully, D. F., Vassilatis, D. K., Liu, K. K., Paress, P. S., Van der Ploeg, L. H. T., Schaeffer, J. M. & Arena, J. P.]. The terminology H (hyperpolarization) receptor is used to distinguish glutamate-gated chloride channels from the excitatory D (depolarization) glutamate receptors of locust muscle [Lea, T. J. & Usherwood, P. N. R. Comp. Gen. Pharmacol. 4, 333–350 (1973)], [Cull-Candy, S. G. J. Physiol. 255, 449–464 (1976)]. Similar to oocytes injected with Dros GluCl RNA, arthropod H-receptors are characteristically activated with ibotenate, blocked with low affinity by picrotoxin, and are not activated with GABA [Lingle, C. & Marder, E. Brain Res. 212, 481–488 (1981)], [Wafford, K. A. & Sattelle, D. B. J. Exp. Biol. 144, 449–462 (1989)], [Cull-Candy, S. G. J. Physiol. 255, 449–464 (1976)], [Lea, T. J. & Usherwood, P. N. R. Comp. Gen. Pharmacol. 4, 351–363 (1973)]. Locust muscle H-receptors are directly activated with avermectins as are the glutamate-gated chloride channels expressed from C. elegans poly $(A)^+$ RNA [Scott, R. H. & Duce, I. R. Pestic, Sci. 16, 599–604 (1985); Arena, J. P., Liu, K. K., Paress, P. S. Schaeffer, J. M. & Cully, D. F. Mol. Brain Res. 15, 339–348 (1992)]. In addition, glutamate-gated chloride channels on locust neuronal soma are potentiated, and directly activated by avermectin [Aydar, E., Harding, L., Beadle, D. J. & Bermudez, I. Proceedings of the British Pharmacological Society p24 (1993)]. Therefore, Dros GluCl appears to be related to arthropod H-receptors. This channel represents the target for avermectins and Compound-1 in Drosophila.

Phylogenetic analyses suggests that Dros GluCl is also related to the C. elegans GluClα and GluClβ channels which represent a unique subclass of ligand-gated chloride channels that may be related to the glycine α and β, Lym ζ and Dros rdl proteins. Although these proteins are phylogenetically related, they respond to different ligands and are pharmacologically distinct [Schmieden, V., Grenningloh, G., Schofield, P. R. & Betz, H. EMBO Journal 8, 695–700 (1989)], [ffrench-Constant, R. H., Rocheleau, T. A., Steichen, J. C. & Chalmers, A. E. Nature 363, 449–451 (1993)], [Grenningloh, G., et al., Neuron 4,963–970 (1990)], [Hutton, M. L, Harvey, R. J. Earley, F. G. P., Barnard, E. A. & Darlison, M. G. FEBS Letters 326, 112–116 (1993)]. Avermectins have been reported to interact with other members of the ligand-gated chloride channel family. In nematodes and insects avermectins block GABA-sensitive current while in crayfish avermectins directly activate a multitransmitter-gated chloride channel (glutamate, acetylcholine, GABA) [Martin, R. J. & Pennington, A. J. Br. J. Pharmacol. 98, 747–756 (1989)], [Zufall, F., Franke, C. & Halt, H. J. Exp. Biol. 142, 191–205 (1989)], [Holden-Dye, L. & Walker, R. J. Parasitology 101, 265–271 (1990)], [Bermudez, I., Hawkins, C. A., Taylor, A. M. & Beadle, D. J. Journal of Receptor Research 11, 221–232 (1991). In oocytes expressing chick brain $GABA_a$ receptors avermectins potentiate the GABA response [Sigel, E. & Baur, R. Mol. Pharmacol. 32,749–752 (1987)]. In addition, avermectins inhibit strychnine binding to mammalian glycine receptors [Graham, D., Pfeiffer, F. & Betz, H. Neurosci. Letters 29, 173–176 (1982)]. However, GluCl proteins are the only members of the ligand-gated chloride channel family that show unique pharmacological characteristics with respect to glutamate and ibotenate, and therefore represent a new subclass of the ligand-gated ion channel family.

The present invention is also directed to methods for screening for compounds which modulate the expression of DNA or RNA encoding GluCl as well as the function of GluCl protein in vivo. Compounds which modulate these activities may be DNA, RNA, peptides, proteins, or non-proteinaceous organic molecules. Compounds may modulate by increasing or attenuating the expression of DNA or RNA encoding GluCl, or the function of GluCl protein. Compounds that modulate the expression of DNA or RNA encoding GluCl or the function of GluCl protein may be detected by a variety of assays. The assay may be a simple "yes/no" assay to determine whether there is a change in expression or function. The assay may be made quantitative by comparing the expression or function of a test sample with the levels of expression or function in a standard sample. Modulators identified in this process are useful as therapeutic agents, insecticides and anthelminthics.

Kits containing GluCl DNA, antibodies to GluCl, or GluCl protein may be prepared. Such kits are used to detect DNA which hybridizes to GluCl DNA or to detect the presence of GluCl protein or peptide fragments in a sample. Such characterization is useful for a variety of purposes including but not limited to forensic analyses and epidemiological studies.

The DNA molecules, RNA molecules, recombinant protein and antibodies of the present invention may be used to screen and measure levels of GluCl DNA, GluCl RNA or GluCl protein. The recombinant proteins, DNA molecules, RNA molecules and antibodies lend themselves to the formulation of kits suitable for the detection and typing of GluCl. Such a kit would comprise a compartmentalized carrier suitable to hold in close confinement at least one container. The carrier would further comprise reagents such as recombinant GluCl protein or anti-GluCl antibodies suitable for detecting GluCl. The carrier may also contain a means for detection such as labeled antigen or enzyme substrates or the like.

Nucleotide sequences that are complementary to the GluCl encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other GluCl antisense oligonucleotide mimetics. GluCl antisense molecules may be introduced into cells by microinjection, liposome encapsulation or by expression from vectors harboring the antisense sequence. GluCl antisense therapy may be particularly useful for the treatment of diseases where it is beneficial to reduce GluCl activity.

GluCl DNA may be used to introduce GluCl into the cells of target organisms. The GluCl gene can be ligated into viral vectors which mediate transfer of the GluCl DNA by infection of recipient host cells. Suitable viral vectors include retrovirus, adenovirus, adeno-associated virus, herpes virus, vaccinia virus, polio virus and the like. Alternatively, GluCl DNA can be transferred into cells by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo GluCl gene therapy. GluCl gene therapy may be particularly useful where it is beneficial to elevate GluCl activity.

Pharmaceutically useful compositions comprising GluCl DNA, GluCl RNA, or GluCl protein, or modulators of GluCl receptor activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose disorders in which modulation of GluCl-related activity is indicated. The effective amount may vary according to a variety of factors such as the individual's condition, weight, sex and age. Other factors include the mode of administration. The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the GluCl receptor or its activity while minimizing any potential toxicity. In addition, co-administration or sequential administration of other agents may be desirable.

The method of the present invention also has the objective of providing suitable topical, oral, systemic and parenteral pharmaceutical formulations for use in the novel methods of treatment of the present invention. The compositions containing compounds identified according to this invention as the active ingredient for use in the modulation of GluCl receptors can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a GluCl modulating agent.

The daily dosage of the products may be varied over a wide range from 0.001 to 1,000 mg per patient, per day. For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The dosages of the GluCl receptor modulators are adjusted when combined to achieve desired effects. On the other hand, dosages of these various agents may be independently optimized and combined to achieve a synergistic result wherein the pathology is reduced more than it would be if either agent were used alone.

Advantageously, compounds active in the method of the present invention may be administered in a single daily dose, or the total daily dosage may be administered in divided doses of two, three or four times daily. Furthermore, compounds active in the method of the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds active in the method of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds active therein can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds active in the method of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds active in the method of the present invention may also be delivered by the use of monoclonal antibodies as individual carriers to which the compound molecules are coupled. The compounds active in the method of the present invention may also be coupled with soluble polymers as targetable drug carriers. Such polymers can include polyvinyl-pyrrolidone, pyran copolymer, polyhydroxy-propylmethacryl-amidephenol, polyhydroxy-ethylaspartamidephenol, or polyethyl-eneoxidepolylysine substituted with palmitoyl residues. Furthermore, the compounds active in the method of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The compounds that are active in the methods of the present invention are useful as antiparastic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostornum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Diseases caused by ectoparasitic arthropods such as ticks, mites, lice, stable flies, hornflies, blowflies, fleas, and other biting insects such as Tenophalides, Ixodes, Psoroptes, Lucilia, and Hemotobia, are also a serious problem. Infection and infestation by these parasites results in loss of blood, skin lesions, and can interfere with normal eating habits thus causing weight loss. These infections can also result in transmission of serious diseases such as encephalitis, anaplasmosis, swine pox, and the like which can be fatal. The compounds that are active in the method disclosed herein are useful for the prevention and treatment of these infections and infestations.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have activity against these parasites, and in addition are also active against Dirofilaria in dogs, Nematospiroides and Syphacia in rodents, biting insects, and migrating diperous larvae such as Hypoderma sp. in cattle, and Gastrophilus in horses.

The compounds active in the method disclosed herein are also useful against endo and ecto parasites which cause parasitic diseases in humans. Examples of such endoparasites which infect man include gastro-intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra-intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The active compounds are active against these endo and ecto parasites and in addition are also active against biting insects and other dipterous pests which annoy humans.

The compounds active in the method disclosed herein are also useful against common household pests such as Blatella sp. (cockroach), Tineola sp. (clothes moth), Attagenus sp. (carpet beetle), *Musca domestica* (housefly) and against *Solenopsis Invicta* (imported fire ant).

The compounds active in the method disclosed herein are furthermore useful against agricultural pests such as aphids (Acyrthiosiphon sp.), locusts, spider mites, and boll weevils as well as against insect pests which attack stored grains such as Tribolium sp. and Tenebrio sp., and against immature stages of insects living on plant tissue. The compounds are also useful as a nematodicide for the control of soil nematodes and plant parasites such as Meloidogyne sp., which may be agriculturally important.

For use as an antiparasitic agent in animals the compounds may be administered internally either orally, or by injection, or topically as a liquid drench or as a shampoo.

For oral administration, the compounds active in the method disclosed herein may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds active in the method disclosed herein may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the compounds active in the method disclosed herein is possible through the use of a liquid drench or a shampoo containing the instant compounds as an aqueous solution, dispersion or suspension. These formulations generally contain a suspending agent such as bentonite, a wetting agent or the like excipient, and normally will also contain an antifoaming agent. Formulations containing from 0.001 to 1% by weight of the active ingredient are acceptable. Preferred formulations are those containing from 0.01 to 1% by weight of the active compounds.

The compounds active in the method disclosed herein are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds may be used individually or in combination with each other or with other unrelated antiparasitic agents. The dosage of the compounds required for best results depends on several factor such as the species and size of the animal, the type and severity of the infection, the method of administration and the compound used. Oral administration of the compounds at a dose level of from 0.0005 to 10 mg per kg of animal body weight, either in a single dose or in several doses spaced a few days apart, generally gives good results. A single dose of one of the compounds normally gives excellent control however repeat doses may be given to combat re-infection or for parasite species which are unusually persistent. The techniques for administering these compounds to animals are known to those skilled in the veterinary field.

The compounds active in the method disclosed herein may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

The following examples illustrate the present invention without, however, limiting the same thereto.

EXAMPLE 1

Drosophila RNA isolation

Poly(A)⁺ RNA was prepared from heads of the Oregon R strain of *Drosophila melanogaster*. The heads were rapidly frozen in liquid $N_2$ and ground with a mortar and pestle while submerged in liquid $N_2$. The frozen, powdered Drosophila tissue was added to a solution containing 4M guanidinium thiocyanate, 5 mM sodium citrate pH 7.0, and 0.1M β-mercaptoethanol (1 gm tissue/10 ml solution), and was mixed with a polytron homogenizer. After 1 minute of homogenization, 0.5% sodium sarkosyl was added and mixed well and the solution was centrifuged at 10,000 rpm for 10 minutes. The supernatant was layered over a 5.7M CsCl cushion and centrifuged for 18 hours at 33,000 rpm. The RNA pellet was washed with 70% ethanol, resuspended in $H_2O$ and extracted with chloroform:isobutanol, 4:1 and precipitated with ethanol. Poly (A)⁺ RNA was isolated by two rounds of purification on oligo (dT)-cellulose columns.

EXAMPLE 2

Cloning and characterization of the Drosophila GluCl PCR product

DNA oligonucleotide primers 5'TGGGT(AGCT)(TA)(CG)(AGCT)TT(CT)TGGTT-3' [SEQ. ID. No.: 1] (Primer 1) and 5'GC(TGCA)CC(TGA)ATCCA(TGCA)AC(GA)TC(TGA)AT-3' [SEQ. ID., No.: 2] (Primer 2) were used in a low stringency PCR reaction to amplify a Drosophila GluCl gene sequence. These oligonucleotides encode the amino acid sequences which are present in the M1 and M3 domains of the C. elegans GluClα gene (Cully et al., supra). Drosophila poly (A)$^+$ RNA (1 ug in 17 µl H$_2$O) was heated at 65° C. 3 min. and placed on ice. The following reagents were added on ice: 3 µl of RNasin (40 u/µl), 8 µl of 5× RT buffer (250 mM Tris-HCl pH 8.3, 375 mM KCl, 15 mM MgCl$_2$, BRL), 4 µl of 0.1M DTT, 4 µl of 20 mM dNTPs, 2 µl of 20 µM Primer 2 oligonucleotide and 0.5 µl of 200 units/µl of Moloney Murine Leukemia virus reverse transcriptase. The reaction was incubated for 90 minutes at 42° C., and the reaction was stopped by heating at 65° C. for 10 min. The first strand cDNA that resulted was used in a polymerase chain reaction as follows: 3 µl of cDNA was incubated in a 50 µl reaction with 2.5 units of AmpliTaq DNA polymerase (Perkin Elmer Cetus) in Taq reaction buffer (1.5 mM MgCl$_2$, 50 mM KCl, 10 mM TrisHCl pH 8.3, 400 µM dNTPs) with 1.2 µM of each primer (DNA sequences 1 and 2) and 20 µCi of $^{32}$P-dCTP. The reaction was incubated in a Perkin Elmer Cetus thermocycler programmed for 25 cycles at 94° (1') 37° (2') 72° (3'). The reaction was mixed with 1 µg of tRNA, 1/10 volume 3M sodium acetate, and 2 volumes of 100% ethanol, incubated at −20° C. 16 hrs, centrifuged 30 min at 11,000×g, and washed with 70% ethanol. The pellet was dried and resuspended in 3 µl H$_2$O and 3 µl of stop solution (95% formamide, 20 mM EDTA, 0.05% Bmmophenol Blue, 0.05% Xylele Cyanol FF), heated at 70° C. 2', and electrophoresed on a 6% acrylamide-urea sequencing gel (Maniatis) until the Xylene Cyanol marker was at the bottom of the gel (40 cm). A control DNA was sequenced (USB Sequenase Version 2.0 DNA sequencing kit) and ran on the gel as size markers. The gel was removed and soaked for 15 min. in 10% methanol; 7% acetic acid, transferred to Whatman 3mm filter paper, dried, and exposed to X-ray film. The gel corresponding to the region of 152 bases was cut out and soaked in 400 µl H$_2$O for 2 hrs at 22° C. The eluted DNA (30 µl) was used as a template in a 100 µl PCR reaction mix containing Taq reaction buffer, 1.0 µM of each primer (DNA sequence 1 and 2) and 5 units of Taq polymerase. The thermocycler program was as above. A 30 µl aliquot of this PCR reaction was used as a template for a second identical PCR reaction.

The 152 bp PCR-amplified DNA fragment was precipitated from the reaction mixture with 1/10 volume 3M sodium acetate and 2 volumes 100% ethanol at −20° C. for 16 hrs., centrifuged 30 min at 11,000×g, and washed with 70% ethanol. The pellet was dried and resuspended in 10 µl TE (Tris-HCl pH 8.0; 1 mMEDTA) and electrophoresed on a 4% NuSieve TAE (40 mMTris-HCl pH 8.0; 20 mM sodium acetate; 2 mMEDTA) agarose gel (FMC BioProducts). The DNA fragment was excised from the gel and purified using a QIAEX gel extraction kit (Qiagen, Inc.). The purified DNA fragment was ligated into the pCR vector using the TA Cloning System (Invitogen Corp.). The ligated DNA was precipitated with 1/10 volume of 3M sodium acetate and 2 volumes of 100% ethanol and incubated at −20° C., centrifuged, washed and resuspended in 2 µl water as described above. A 1 µl aliquot of DNA was transformed into 40 µl INVαF' electro-competent cells (Invitrogen Corp) by electroporation using a Gene-Pulser (BioRad) at 2.5 KV, 25 µF capacitance, and 200 ohms resistance, after which 1 ml of SOC medium (Sambrook, J., Fritsch, E. F., Maniatis, T. in Molecular Cloning: A Laboratory Manual, Second Edition, Cold Spring Harbor Laboratory Press, Cold Spring Harbor, N.Y. 1989) was added and the cells were incubated for 1 hr at 37° C. The transformed cells were plated on LB agar plates containing 50 µg/ml ampicillin and 40 µg/ml X-gal (5-bromo-4-chloro-3-indolyl-β-D-galactoside) and incubated 18 hrs. at 37° C. White colonies were picked and ten of these, each containing a vector with an insert of approximately 152 base pairs, were sequenced using a USB Sequenase Version 2.0 DNA sequencing kit. Clone pPCR-2 was chosen as a probe to identify a full length cDNA clone. The DNA sequence of pPCR-2 is SEQ. ID. No.: 4, which codes for a peptide of predicted amino acid sequence: W V T F W L D Q G A V P A R V S L G V T T L L T - MATQTSGINASLPP VSYTKAIDVWIG. [SEQ. ID. No.: 3]

EXAMPLE 3

Isolation and identification of the Dros GluCl cDNA

A cDNA library was made from heads of the Oregon R strain of Drosophila in the phagemid cloning vector (Stratagene). This library was transfected into E. coli BB4 cells, plated on NZY medium (Sambrook, J., Fritsch, E. F., Maniatis, T. in Molecular Cloning: A Laboratory Manual, Second Edition, Cold Spring Harbor Laboratory Press, Cold Spring Harbor, N.Y. 1989.), and incubated 18 hrs. at 37° C. The resultant plaques were transferred to Durulose membranes (Stratagene). The membranes were prehybridized in prehybridization solution (50% formamide; 2× Denhardts reagent; 5× SSPE; 0.1% SDS; 100 µg/ml single stranded herring sperm DNA) for 16 hrs. at 42° C., and hybridized for 65 hrs. at 42° C. in 50 ml hybridization solution (prehybridization solution containing 10% dextran sulfate) containing 2×10$^7$ cpm of the EcoRI insert fragment of Clone pPCR-2 which was labeled with $^{32}$P-dCTP by random priming using a Random Primed DNA Labeling Kit (Boehringer Mannheim). The membranes were exposed to X-ray film. Thirty-six positive phage clones were identified and were converted into plasmids by in vivo excision as per the Stratagene protocol. One clone, pDros GluCl was found to contain an insert of 3958 bases. The sequence of Dros GluCl cDNA is shown in FIG. 1.

EXAMPLE 4

Prima Structure of the Dros GluCl Channel

The nucleotide sequence of pDros GluCl revealed a single large open reading frame of about 1518 base pairs. The cDNA has a 5' untranslated extension of about 254 nucleotides and a 3' untranslated region of about 2186 nucleotides. The first in-frame methionine (base 405) was designated as the initiation codon for the open reading frame that ends at the stop codon TAA (base 1773). The predicted GluCl protein (FIG. 2) has an estimated molecular mass (M$_r$) of about 52,344 daltons. The protein contains hydrophobic amino-terminal residues with sequences highly predictive of signal cleavage sites that would result in a mature protein initiating at about amino acid 23.

The predicted Dros GluCl protein was aligned with nucleotide and protein databases and found to be related to the C. elegans GluClα, GluClβ, and to the glycine and GABA$_A$ receptors. The conserved motifs found in this family of channels, such as a large NH$_2$-terminal extracellular domain and the four hydrophobic transmembrane domains M1 through M4, were also found in the Dros GluCl sequences. The Dros GluCl protein contained the conserved cysteine residues found in the extracellular domain of all ligand-gated chloride channels. Two additional cysteine residues (amino acids 356 and 367) were present that are also found in glycine-gated chloride channels and the GluClα and GluClβ of *C. elegans*. The Dros GluCl protein contained two strong consensus sequences for protein kinase C phosphorylation sites located between the putative membrane spanning domains M3 and M4. In GABA$_A$ receptor proteins, similar phosphorylation sites are located in the intracellular domain between M3 and M4 and are believed to play a role in channel regulation s [Leidenheimer, N. J., McQuilkin, S. J., Hahner, L. D., Whiting, P. & Harris, R. A. *Mol. Pharm.* 41, 1116–1123 (1992), [Kellenberger, S., Malherbe, P. & Sigel, E. *J. Biol. Chem.* 267, 24660–25663 (1992)]. As found in GABA$_A$ and glycine receptor sequences, the GluCl protein contained putative N-linked glycosylation sites in the proposed extracellular domain.

Figure 5:
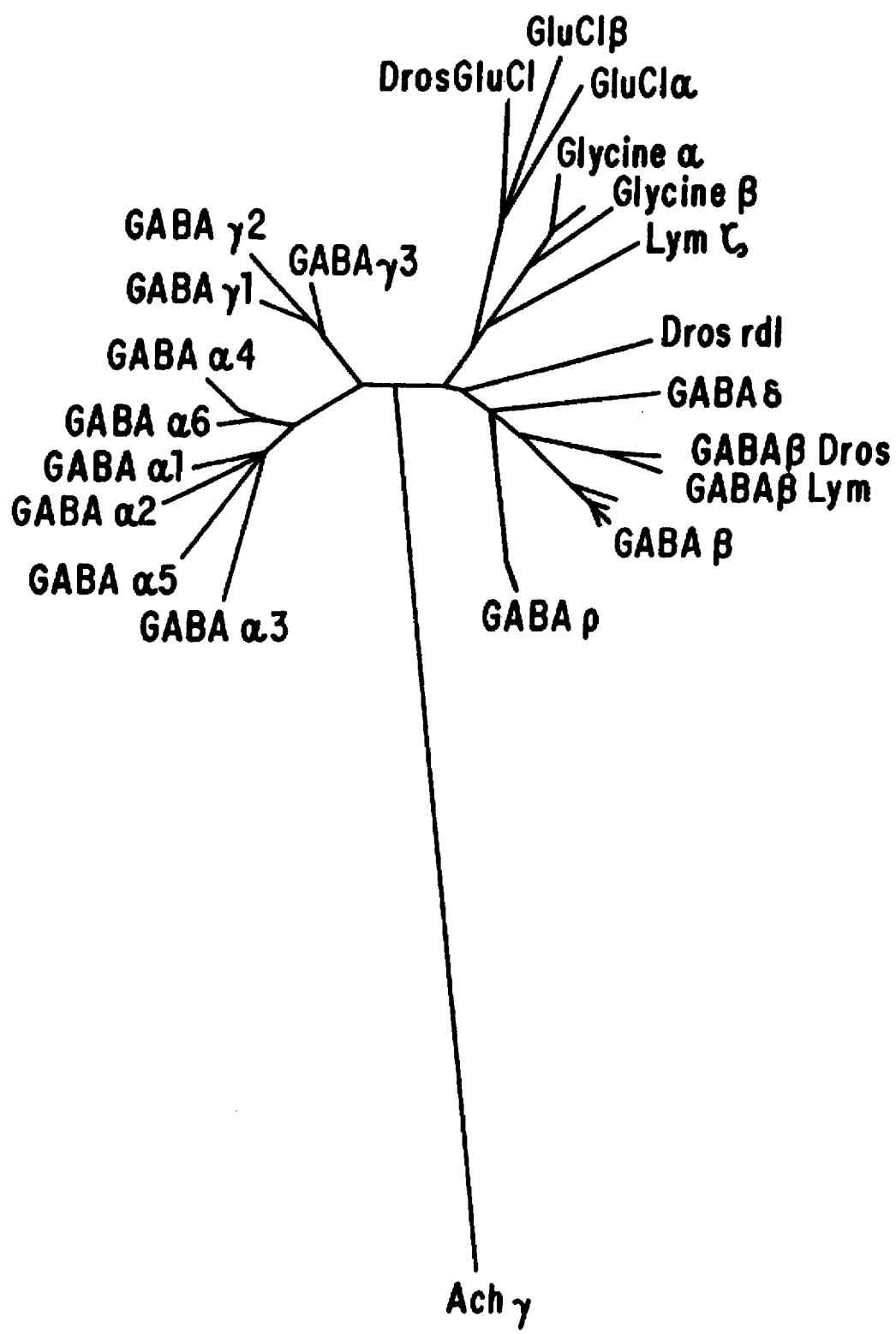
FIG. 5 A phylogenetic analysis of Dros GluCl is shown.

A phylogenetic analysis was performed with the entire Dros GluCl protein sequence, the *C. elegans* GluClα and GluClβ proteins the GABA$_A$ and glycine receptor proteins, and related invertebrate protein sequences (FIG. 5). A discrete evolutionary division in this family of proteins was shown by a divergence into two major branches resulting in the division of the GABA$_A$ α and γ proteins from the remaining proteins. Within these major branches are sub-branches that group the proteins into the respective subclasses, such as the GABA$_A$ α, β, γ, δ, ρ, and glycine α and β.

Although the Dros GluCl protein is phylogenetically related to the *C. elegans* GluClα and GluClβ, glycine α and β, Lym ζ and Dros rdl proteins, they are pharmacologically distinct and group with the GluCl proteins. Expression studies in Xenopus oocytes show that functional homomeric chloride channels are formed by the glycine α proteins that are sensitive to glycine [Schmieden, V., Grenningloh, G., Schofield, P. R. & Betz, H. *EMBO Journal* 8, 695–700 (1989)] and the Dros rdl protein that is sensitive to GABA [ffrench-Constant, R. H., Rocheleau, T. A., Steichen, J. C. & Chalmers, A. E. *Nature* 363, 449–451 (1993)]. Homomeric glycine β channels are formed at very low efficiency [Grenningloh, G., et al., *Neuron* 4, 963–970 (1990)], and the Lym ζ protein does not form functional homomeric channels [Hutton, M. L., Harvey, R. J., Earley, F. G. P., Barnard, E. A. & Darlison, M. G. *FEBS letters* 326, 112–116 (1993)].

EXAMPLE 5

Expression of the Dros GluCl protein in Xenopus oocytes

Clone pDros GluCl was linearized by digestion with the restriction endonuclease SalI. In vitro RNA was synthesized from 0.5 μg of this plasmid in a reaction containing 40 mM Tris-HCl, pH 7.5; 6 mM MgCl$_2$; 2 mM Spermidine; 10 mM NaCl; 10 mM DTT; 0.05 mg/ml Bovine Serum Albumin; 2 units/ul RNasin; 800 μM each ATP, CTP, and UTP; 200 μMGTP; 800 μM m7G(5')ppp(5')G; 5 μCi $^{32}$P-CTp; and 50 units T3 RNA polymerase in a final volume of 50 μl. The reaction was incubated for 3 hours at 37° C. followed by an additional 15 minutes incubation with 20 units RNase free DNase and extraction with phenol, phenol:chloroform, and chloroform. The RNA was precipitated with 1/10 volume 3M sodium acetate and 2.5 volumes 100% ethanol, stored at −20° C. for 16 hours, washed with 70% ethanol and resuspended in water at a concentration of 1 mg/ml for injection into Xenopus laevis oocytes.

*Xenopus laevis* oocytes were prepared and injected using standard methods previously described and known in the art [Arena, J. P., Liu, K. K., Paress, P. S. & Cully, D. F. *Mol. Pharmacol.* 40, 368–374 (1991); Arena, J. P., Liu, K. K., Paress, P. S., Schaeffer, J. M. & Cully, D. F. *Mol. Brain Res.* 15, 339–348 (1992)]. Adult female *Xenopus laevis* were anesthetized with 0.17% tricaine methanesulfonate and the ovaries were surgically removed and placed in a dish consisting of (mM): NaCl 82.5, KCl 2, MgCl$_2$ 1, CaCl$_2$ 1.8, HEPES 5 adjusted to pH 7.5 with NaOH (OR-2). Ovarian lobes were broken open, rinsed several times, and gently shaken in OR-2 containing 0.2% collagenase (Sigma, Type 1A) for 2–5 hours. When approximately 50% of the follicular layers were removed, Stage V and VI oocytes were selected and placed in media consisting of (mM): NaCl 86, KCl 2, MgCl$_2$ 1, CaCl$_2$ 1.8, HEPES 5, Na pyruvate 2.5, theophylline 0.5, gentamicin 0.1 adjusted to pH 7.5 with NaOH (ND-96) for 24–48 hours before injection. Oocytes were injected with 50 nl of Dros GluCl RNA (0.01–1 mg/ml). Control oocytes were injected with 50 nl of water. Oocytes were incubated for 2–10 days in ND-96 before recording. Incubations and collagenase digestion were carried out at 18° C.

Recordings were made at room temperature in standard frog saline consisting of (mM): NaCl 115, KCl 2, MgCl$_2$ 1, CaCl$_2$ 1.8, HEPES 10, adjusted to pH 7.5 with NaOH. Oocytes were voltage-clamped using a standard two microelectrode amplifier (Dagan 8500 or TEV-200, Minneapolis, Minn.). Pipettes were filled with 3M KCl and had resistances between 0.5–3.0 megaohms. A plexiglass recording chamber (volume 200 μl) was constantly perfused at a rate of 10 ml/min. The recording chamber was connected to ground with a Ag/AgCl electrode. Data were acquired and analyzed using PCLAMP with a TL-1 interface (Axon Instruments, Foster City, Calif.). Membrane current at a holding potential of −80 mV was recorded. The amplitude of drug-sensitive current was determined by subtracting the holding current at −80 mV from from the peak current obtained in the presence of drug. Data were filtered at 30 Hz and sampled at 16.6 Hz. Current/voltage relationships (I/V) and reversal potentials (E$_{rev}$) were determined using a 1–3 sec voltage ramp over the voltage range of −110 to +80 mV. For the ramps, data were filtered at 0.3–3 kHz and sampled at 160 Hz. Current in drug free solution was subtracted from current in the presence of drug to obtain drug-sensitive current/voltage relationships.

Oocytes expressing Dros GluCl protein exhibited a rapidly activating and rapidly desensitizing glutamate-sensitive current (FIG. 4). The EC$_{50}$ for glutamate was 30 μM with a Hill coefficient of 1.3. The rate of densensitization was dependent on the concentration of glutamate becoming faster at higher glutamate concentrations.

IVMPO$_4$ also directly activated current in oocytes expressing Dros GluCl (FIG. 3). Activation of current with IVMPO$_4$ was irreversible for up to 10 minutes after washing IVMPO$_4$ from the bath. Current was maximally activated with 1 μM IVMPO$_4$, and 10 nM activated 20–40% of maximal current.

The insecticide Compound-1 (FIG. 4) as fully described in U.S. Pat. No. 5,399,582 also directly activated membrane current (FIG. 3). Current elicited with Compound-1 was slowly reversible, taking up to 10 minutes to fully return to baseline.

Dros GluCl was also reversibly activated with the glutamate analog ibotenate (maximal activation with 100 μM), and with the related amino acid aspartate (8% of maximal activation with 1 mM). Oocytes injected with Dros GluCl RNA were insensitive to GABA, glycine, kainate, histamine, and N-methyl-D-aspartic acid tested at concentrations of 1 mM or higher. The current elicited with IVMPO$_4$ was blocked weakly with the ligand-gated chloride channel blocker picrotoxin (13% block at 500 µM).

EXAMPLE 6

Cloning of the Dros GluCl cDNA into *E. coli* Expression Vectors

Recombinant Dros GluCl protein is produced in *E. coli* following the transfer of the GluCl expression cassette into *E. coli* expression vectors, including but not limited to, the pET series (Novagen). The pET vectors place Dros GluCl expression under control of the tightly regulated bacteriophage T7 promoter. Following transfer of this construct into an *E. coli* host which contains a chromosomal copy of the T7 RNA polymerase gene driven by the inducible lac promoter, expression of Dros GluCl is induced when an appropriate lac substrate (IPTG) is added to the culture. The levels of expressed Dros GluCl are determined by the assays described above.

The cDNA encoding the entire open reading frame for Dros GluCl is inserted into the NdeI site of pET [16]11a. Constructs in the positive orientation are identified by sequence analysis and used to transform the expression host strain BL21. Transformants are then used to inoculate cultures for the production of Dros GluCl protein. Cultures may be grown in M9 or ZB media, whose formulation is known to those skilled in the art. After growth to an OD$_{600}$=1.5, expression of Dros GluCl is induced with 1 mM IPTG for 3 hours at 37° C.

EXAMPLE 7

Expression of Dros GluCl in Mammalian Cell Lines

The Dros GluCl cDNA was subcloned into the mammalian expression vectors pMAMneo and pcDNA3. pMAMneo was digested with the restriction endonuclease NheI and treated with Klenow enzyme to fill in the 5' overhang. The DNA was then digested with SalI to create a linear vector with one blunt end and one SalI site, and was treated with calf intestine alkaline phosphatase to prevent self ligation. The vector was gel purified on a 0.7% agarose gel. pDros GluCl was digested with SmaI and SalI to remove the insert from the vector, and then run on a 0.7% agarose gel to purify the insert. The insert containing the cDNA was ligated to the purified pMAMneo vector and recombinants were selected and used to transfect mammalian L-cell by CaPO$_4$ precipitation.

pcDNA3 was digested with NotI and treated with Klenow enzyme to fill in the 5' overhang. The DNA was then digested with BamHI to create a linear vector with one blunt end and one BamHI site, and was treated with calf intestine alkaline phosphatase to prevent self ligation. pDros GluCl was digested with SalI and treated with Klenow enzyme to fill in the 5' overhang. The DNA was then digested with BamHI to create a cDNA fragment with one blunt end and one BamHI site, compatable with the pcDNA3 vector. Both the vector and the insert were gel purified on a 0.7% agarose gel and were then ligated together. Recombinants were selected and used to transfect mammalian L-cell by CaPO$_4$ precipitation.

Stable cell clones were selected by growth in the presence of G418. Single G418 resistant clones were isolated and shown to contain the intact Dros GluCl gene. Clones containing the Dros GluCl cDNAs are analyzed for expression using immunological techniques, such as immuneprecipitation, Western blot, and immunofluorescence using antibodies specific to the GluCl proteins. Antibody is obtained from rabbits innoculated with peptides that are synthesized from the amino acid sequence predicted from the Dros GluCl sequences. Expression is also analyzed using patch clamp electrophysiological techniques, an anion flux assay, and $^3$H-ivermectin and $^3$H-glutamate binding assays.

Cells that are expressing Dros GluCl stably or transiently, are used to test for expression of avermectin, glutamate, Compound-1 sensitive chloride channels and for ligand binding activity. These cells are used to identify and examine other compounds for their ability to modulate, inhibit or activate the avermectin, glutamate Compound-1 sensitive chloride channel and to compete for binding with radioactive avermectin, glutamate, Compound-1 derivatives. These cells are used to identify and examine other compounds which modulate GluCl activity with an anion flux assay.

Cassettes containing the Dros GluCl cDNA in the positive orientation with respect to the promoter are ligated into appropriate restriction sites 3' of the promoter and identified by restriction site mapping and/or sequencing. These cDNA expression vectors are introduced into fibroblastic host cells for example COS-7 (ATCC# CRL 1651), and CV-1 tat [Sackevitz et al., *Science* 238: 1575 (1987)], 293, L (ATCC# CRL6362)] by standard methods including but not limited to electroporation, or chemical procedures (cationic liposomes, DEAE dextran, calcium phosphate). Transfected cells and cell culture supernatants can be harvested and analyzed for Dros GluCl expression as described herein.

All of the vectors used for mammalian transient expression can be used to establish stable cell lines expressing Dros GluCl. Unaltered Dros GluCl cDNA constructs cloned into expression vectors are expected to program host cells to make Dros GluCl protein. In addition, Dros GluCl is expressed extracellularly as a secreted protein by ligating Dros GluCl cDNA constructs to DNA encoding the signal sequence of a secreted protein. The transfection host cells include, but are not limited to, CV-1-P [Sackevitz et al., *Science* 238: 1575 (1987)], tk-L [Wigler, et al., *Cell* 11: 223 (1977)], NS/O, and dHFr-CHO [Kaufman and Sharp, *J. Mol. Biol.* 159: 601, (1982)].

Co-transfection of any vector containing Dros GluCl cDNA with a drug selection plasmid including, but not limited to G418, aminoglycoside phosphotransferase; hygromycin, hygromycin-B phosphotransferase; APRT, xanthine-guanine phosphoribosyl-transferase, will allow for the selection of stably transfected clones. Levels of Dros GluCl are quantitated by the assays described herein.

GluCl cDNA constructs are also ligated into vectors containing amplifiable drug-resistance markers for the production of mammalian cell clones synthesizing the highest possible levels of Dros GluCl. Following introduction of these constructs into cells, clones containing the plasmid are selected with the appropriate agent, and isolation of an over-expressing clone with a high copy number of plasmids is accomplished by selection with increasing doses of the agent.

The expression of recombinant Dros GluCl is achieved by transfection of full-length Dros GluCl cDNA into a mammalian host cell.

EXAMPLE 8

Cloning of Dros GluCl cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing Dros GluCl cDNA is produced by the following standard methods (InVitrogen Maxbac Manual): the Dros GluCl cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., *Nuc. Acid. Res.* 18: 5667 (1990)] into Sf9 cells. Recombinant pAC360 viruses are identified by the absence of inclusion bodies in infected cells and recombinant pBlueBac viruses are identified on the basis of β-galactosidase expression (Summers, M. D. and Smith, G. E., Texas Agriculture Exp. Station Bulletin No. 1555). Following plaque purification, Dros GluCl expression is measured by the assays described herein.

The cDNA encoding the entire open reading frame for Dros GluCl is inserted into the BamHI site of pBlueBacII. Constructs in the positive orientation are identified by sequence analysis and used to transfect Sf9 cells in the presence of linear AcNPV mild type DNA.

Authentic, active Dros GluCl is found in the cytoplasm of infected cells. Active Dros GluCl is extracted from infected cells by hypotonic or detergent lysis.

EXAMPLE 9

Cloning of Dros GluCl cDNA into a yeast expression vector

Recombinant Dros GluCl is produced in the yeast *S. cerevisiae* following the insertion of the optimal Dros GluCl cDNA cistron into expression vectors designed to direct the intracellular or extracellular expression of heterologous proteins. In the case of intracellular expression, vectors such as EmBLyex4 or the like are ligated to the Dros GluCl cistron [Rinas, U. et al., *Biotechnology* 8: 543–545 (1990); Horowitz B. et al., *J. Biol. Chem.* 265: 4189–4192 (1989)]. For extracellular expression, the Dros GluCl cistron is ligated into yeast expression vectors which fuse a secretion signal (a yeast or mammalian peptide) to the $NH_2$ terminus of the Dros GluCl protein [Jacobson, M. A., *Gene* 85: 511–516 (1989); Riett L. and Bellon N. *Biochem.* 28: 2941–2949 (1989)].

These vectors include, but are not limited to pAVE1>6, which fuses the human serum albumin signal to the expressed cDNA [Steep O. *Biotechnology* 8: 42–46 (1990)], and the vector pL8PL which fuses the human lysozyme signal to the expressed cDNA [Yamamoto, Y., *Biochem.* 28: 2728–2732)]. In addition, Dros GluCl is expressed in yeast as a fusion protein conjugated to ubiquitin utilizing the vector pVEP [Ecker, D. J., *J. Biol. Chem.* 264: 7715–7719 (1989), Sabin, E. A., *Biotechnology* 7: 705–709 (1989), McDonnell D. P., *Mol. Cell Biol.* 9: 5517–5523 (1989)]. The levels of expressed Dros GluCl are determined by the assays described herein.

EXAMPLE 10

Purification of Recombinant Dros GluCl

Recombinantly produced Dros GluCl may be purified by antibody affinity chromatography.

Dros GluCl antibody affinity columns are made by adding the anti-Dros GluCl antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized Dros GluCl are slowly passed through the column. The column is then washed with phosphate-buffered saline together with detergents until the optical density (A280) fails to background, then the protein is eluted with 0.23M glycine-HCl (pH 2.6) together with detergents. The purified Dros GluCl protein is then dialyzed against phosphate buffered saline.

---

What is claimed is:

1. A purified DNA molecule encoding a Drosophila avermectin and/or glutamate binding protein which functions as a glutamate-gated anion channel wherein said protein comprises the amino acid sequence set forth in SEQ ID NO:6.

2. An expression vector for expressing a Drosophila avermectin and/or glutamate binding protein in a recombinant host cell wherein said expression vector comprises the DNA molecule of claim 1.

3. A host cell which expresses a recombinant a Drosophila avermectin and/or glutamate binding protein wherein said host cell contains the expression vector of claim 2.

4. A process for the expression of a Drosophila avermectin and/or glutmate binding protein, comprising:

(a) transfecting the expression vector of claim 2 into a suitable host cell; and, (b) culturing the host cells under conditions suitable for expression of said Drosophila avermectin and/or glutamate binding protein from said expression vector.

5. A purified DNA molecule encoding a Drosophila avermectin and/or glutamate binding protein which functions as a glutamate-gated anion channel wherein said protein consists of the amino acid sequence set forth in SEQ ID NO:6.

6. An expression vector for expressing a Drosophila avermectin and/or glutmate binding protein in a recombinant host cell wherein said expression vector comprises the DNA molecule of claim 5.

7. A host cell which expresses a recombinant a Drosophila avermectin and/or glutamate binding protein wherein said host cell contains the expression vector of claim 6.

8. A process for the expression of a Drosophila avermectin and/or glutamate binding protein, comprising:
   (a) transfecting the expression vector of claim 6 into a suitable host cell; and,
   (b) culturing the host cells under conditions suitable for expression of said Drosophila avermectin and/or glutamate binding protein from said expression vector.

9. A purified DNA molecule encoding a Drosophila avermectin and/or glutamate binding protein which functions as a glutamate-gated anion channel wherein said DNA molecule comprises the nucleotide sequence set forth in SEQ ID NO:5.

10. An expression vector for expressing a Drosophila avermectin and/or glutamate binding protein in a recombinant host cell wherein said expression vector comprises the DNA molecule of claim 9.

11. A host cell which expresses a recombinant a Drosophila avermectin and/or glutamate binding protein wherein said host cell contains the expression vector of claim 10.

12. A process for the expression of a Drosophila avermectin and/or glutamate binding protein, comprising:
   (a) transfecting the expression vector of claim 9 into a suitable host cell; and,
   (b) culturing the host cells under conditions suitable for expression of said Drosophila avermectin and/or glutamate binding protein from said expression vector.

13. A purified DNA molecule encoding a Drosophila avermectin and/or glutamate binding protein which functions as a glutamate-gated anion channel wherein said DNA molecule consists of the nucleotide sequence set forth in SEQ ID NO:5.

14. An expression vector for expressing a Drosophila avermectin and/or glutamate binding protein in a recombinant host cell wherein said expression vector comprises the DNA molecule of claim 9.

15. A host cell which expresses a recombinant a Drosophila avermectin and/or glutamate binding protein wherein said host cell contains the expression vector of claim 10.

16. A process for the expression of a Drosophila avermectin and/or glutamate binding protein, comprising:
   (a) transfecting the expression vector of claim 9 into a suitable host cell; and,
   (b) culturing the host cells under conditions suitable for expression of said Drosophila avermectin and/or glutamate binding protein from said expression vector.

* * * * *